United States Patent [19]
Bolton et al.

[11] Patent Number: 5,945,291
[45] Date of Patent: Aug. 31, 1999

[54] METHOD FOR DISTINGUISHING VIABLE, EARLY APOPTOTIC, LATE APOPTOTIC, AND NECROTIC CELLS

[75] Inventors: Wade E. Bolton, Plantation; Steven K. Koester, Pembroke Pines, both of Fla.

[73] Assignee: Coulter International Corp., Miami, Fla.

[21] Appl. No.: 08/966,937

[22] Filed: Nov. 10, 1997

[51] Int. Cl.$^6$ .................................................... G01N 33/53

[52] U.S. Cl. ........................... 435/7.1; 435/7.8; 436/501; 436/548; 436/800; 530/387.1; 530/388.1

[58] Field of Search ..................... 435/7.1, 7.21, 435/7.8; 436/501, 548, 800; 530/387.1, 388.1

[56] References Cited

PUBLICATIONS

Vermes et al (1995) Journal of Immunological Methods vol. 184 No. 1 pp. 39–51.
J. Ameisen et al, *Immunol. Today*, 12:102–105 (1991).
J. Kerr et al, *Br. J. Cancer*, 26:239 (1972).
A. Wyllie, *Nature*, 284:555 (1980).
C. Zhang et al, *J. Immunol.*, 157:3980–3987 (1996).
I. Schmid et al, *Cytometry*, 15:12–20 (1994).
O'Brien et al, *Cytometry*, 28:81–89 (1997).

*Primary Examiner*—Paula K. Hutzell
*Assistant Examiner*—Geetha P. Bansal
*Attorney, Agent, or Firm*—Cathy A. Kodroff

[57] ABSTRACT

The present invention provides a method for distinguishing between viable, early apoptotic, late apoptotic and necrotic cells utilizing multi-color immunofluorescence.

19 Claims, 1 Drawing Sheet

Negative Gate

Positive Gate

METHOD FOR DISTINGUISHING VIABLE, EARLY APOPTOTIC, LATE APOPTOTIC, AND NECROTIC CELLS

FIELD OF THE INVENTION

This invention relates generally to assays useful in the detection of apoptotic cells.

BACKGROUND OF THE INVENTION

Apoptosis has been proposed as a mechanism for the T-cell depletion seen in individuals infected with HIV [J. C. Ameisen and A. Capron, *Immunol. Today*, 12:102–105 (1991)], as well as individuals having other pathological conditions. Apoptosis is accompanied by characteristic morphologic changes and the degradation of DNA into internucleosomal fragments in cells [J. F. R. Kerr et al, *Br. J. Cancer*, 26:239 (1972); A. H. Wyllie, *Nature*, 284:555 (1980)]. Recent evidence has indicated that before the occurrence of morphologic changes and death itself in the spontaneous or induced apoptosis, the cells undergo substantial alterations in both phenotypic and functional properties. These include an activation of endogenous endonucleases, the expression of molecular markers, and a loss or increase in protein expression [C. Zhang et al, *J. Immunol.*, 157:3980–3987 (1996)]. Although molecular alterations are closely associated with apoptosis, their precise role in the process of apoptotic cell death remains to be understood.

In an effort to detect apoptotic cells, several different assays and assay reagents have been utilized. Apoptotic cells can be visualized by flow cytometry using fluorescent DNA stains [I. Schmid et al, *Cytometry*, 15:12–20 (1994)], DNA agarose gel electrophoresis [A. H. Wyllie, cited above], or by in situ nick translation [R. R. Jonker et al., *NATO ASI Series*, H67:355–362 (1993)]. However, these assays and reagents have not proved adequate for distinguishing cells from early stages of apoptosis from those which are late apoptotic and necrotic. For example, the use of anti-tubulin antibody, which stains the intracellularly-located microtubules, has been described. [O'Brien et al, *Cytometry*, 28:81–89 (1997)]. However, this antibody is not specific for apoptotic cells, but rather recognizes any cell having a disrupted membrane.

What is needed in the art is an efficient method for identifying and distinguishing early apoptotic and late apoptotic/necrotic cells.

SUMMARY OF THE INVENTION

The method of the invention involves providing a first binding protein specific for an apoptotic-associated antigen labeled with a first visually detectable label, a second binding protein specific for an apoptotic-associated antigen labeled with a second visually detectable label, and a third binding protein specific for an intracellular antigen common to eukaryotic cells labeled with third visually detectable label, wherein said first, second, and third visually detectable labels are distinguishable; contacting a sample of cells with the labeled eukaryotic binding protein, thereby providing positive and negative labeled eukaryotic binding protein populations; contacting the cells with the first labeled binding protein; permeabilizing the cells; staining the cells with the second labeled binding protein; and analyzing the cells to identify viable cells, early apoptotic cells, late apoptotic cells, and necrotic cells. Desirably, the apoptotic-associated antigen is the 7A6 antigen and the first and/or second binding protein is an antibody or fragment thereof which specifically binds to the 7A6 antigen.

In a currently preferred embodiment, the invention provides a method involving the steps of contacting a sample of cells with anti-tubulin-FITC, thereby providing positive and negative anti-tubulin-FITC populations; contacting the cells with APO2.7-PE; permeabilizing the cells with digitonin; staining the cells with APO2.7-PECy5; and analyzing the cells by flow cytometry to distinguish viable cells, early apoptotic cells, late apoptotic cells, and necrotic cells.

Other aspects and advantages of the present invention are described further in the following detailed description of the preferred embodiments thereof

BRIEF DESCRIPTION OF THE DRAWINGS

FIG. 1A is a histogram illustrating light scatter from the cells to be analyzed.

DETAILED DESCRIPTION OF THE INVENTION

Figure 1B:
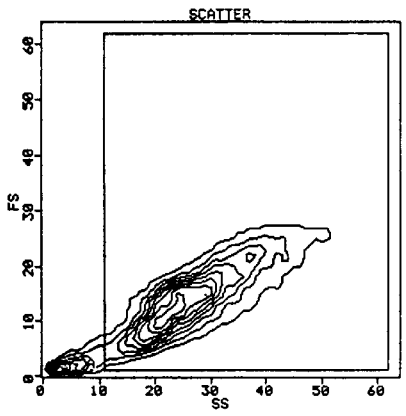
FIG. 1B is a histogram illustrating the results of anti-tubulin staining following performance of the method of the invention and gating on light scatter.
Figure 1B:
Figure 1B:
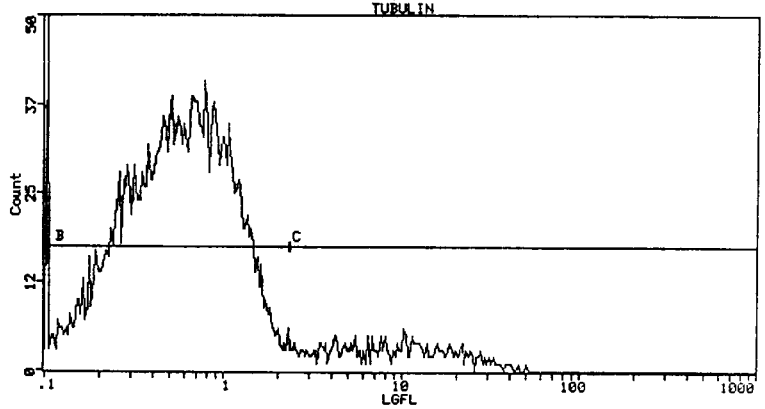

The present invention provides an efficient method for identifying and distinguishing viable cells, early apoptotic cells, late apoptotic cells, and necrotic cells.

Suitable samples may be obtained from a veterinary or human patient and include, but are not limited to, whole blood, plasma, serum, urine, and disaggregated tissues, which may be prepared by techniques known to the skilled artisan. Such samples include cells suspected of being in early or late apoptosis, and may also include viable and necrotic cells.

As described in more detail below, the method of the invention involves the steps of contacting a sample of cells (e.g., peripheral blood lymphocytes from an HIV-infected patient) with labeled anti-tubulin, to provide positive and negative anti-tubulin populations. These populations are detectable, preferably visually, and most preferably colorimetrically, by virtue of the label associated with the anti-tubulin.

According to the method of the invention, anti-tubulin is preferably used to detect cells that have disrupted cell membranes and will be referred to, for convenience, throughout the specification. However, the skilled artisan will readily understand that other binding proteins which are specific for eukaryotic proteins may be substituted for anti-tubulin. Examples of suitable molecules which may be substituted for anti-tubulin include binding proteins for cytokeratin, actin, other microtubule-associated proteins, and other intracellular proteins which are ubiquitous and constitutively expressed in eukaryotic cells. Such proteins are well known, and may be produced using known techniques, or purchased from a variety of sources, e.g, DAKO [Sweden].

By "contacting" is generally meant that the binding protein is introduced into the sample in a test tube, flask, tissue culture or the like, and incubated at a temperature and time sufficient to permit the binding protein (e.g., anti-tubulin or APO2.7) to bind to a cell or a fraction thereof containing the target. In general, when utilizing the preferred analysis method of flow cytometry, cells for staining are aliquoted at $0.5 \times 10^6$/test, into 12×75 mm tubes, centrifuged for 5 minutes at 200×g, and the supernate discarded. Fluorescently conjugated antibodies at predetermined concentrations (antibody concentrations are predetermined by titration), are added to cells that are resuspended in PBSF (phosphate buffered saline with 2.5% fetal calf serum) to a total volume of 100 $\mu$l, and are incubated for 15 minutes at room temperature (RT), protected from the light. All washes are accomplished by resuspending cells in 2.0 ml of PBSF, centrifuging at 200×g for 5 minutes, and discarding the supernate. Other methods for contacting the samples with the binding protein are useful and may be selected depending on the type of assay protocol to be run. Suitable assays are discussed in more detail below.

As used herein, the term "label" refers to a molecule which may be conjugated or otherwise attached (i.e., covalently or non-covalently) to a binding protein (e.g., anti-tubulin or APO2.7) as defined herein. Particularly suitable labels include those which permit analysis by flow cytometry, e.g., fluorochromes. Preferred fluorochromes include phycoeyrthin (P.E., Coulter Corp., Hialeh, Fla.), phycoerythrin-cyanin dye 5 (PECy5, Coulter), and fluorescein isothiocyanate (FITC, International Biological Supplies, Melbourne, Fla.). Other suitable detectable labels include those useful in colorimetric enzyme systems, e.g., horseradish peroxidase (HRP) and alkaline phosphatase (AP). Other proximal enzyme systems are known to those of skill in the art, including hexokinase in conjunction with glucose-6-phosphate dehydrogenase. Chemiluminescent labels, such as green fluorescent proteins, blue fluorescent proteins, and variants thereof are known. Also bioluminescence or chemiluminescence can be detected using, respectively, NAD oxidoreductase with luciferase and substrates NADH and FMN or peroxidase with luminol and substrate peroxide. Other suitable label systems useful in the present invention include radioactive compounds or elements, or immunoelectrodes. The labels used may be readily selected by one of skill in the art and are not a limitation on the present invention. However, it is preferred that, regardless of the labels used, the labels used to mark the anti-tubulin, the first apoptosis-associated antigen and the second apoptosis-associated antigen be distinguishable from one another, and thus, allow cells stained with these labels to be distinguished.

The term binding protein refers to proteins which specifically bind to a selected target, e.g., an antigen. The binding protein specific for an apoptotic-associated antigen is preferably an antibody or a fragment thereof which retains the binding specificity of the antibody from which it is derived. Most preferably, these antibodies are monoclonal antibodies, although polyclonal antibodies may also be utilized. Suitable antibody fragments include, e.g., F(ab')2 fragments, Fab', Fv fragments, synthetic antibodies containing the antibody complementarity determining regions. Suitable techniques, including digestion of the antibody or recombinant production methods, for obtaining these proteins are well known to those of skill in the art.

As stated above, in the method of the invention binding proteins specific for one or more apoptotic-associated antigens are utilized. Desirably, such an antigen is detectable during apoptosis, but not in normal cells. Most desirably, the antigen is not detectable in cells with disrupted membranes which are not undergoing apoptosis and is a soluble protein. An example of another suitable apoptotic-associated antigen is phosphatidylserine; others suitable antigens can be determined by one of skill in the art.

In a currently preferred embodiment, the apoptotic-associated antigen is the 7A6 antigen, a 38 kD protein which is detected on the mitochondrial membrane in cells undergoing apoptosis, but is not detected on the normal cell surface or in permeabilized cells not undergoing apoptosis. Making use of this 38 kD antigen, antibodies specific for the 7A6 antigen may be readily generated using this antigen and known techniques. This antigen is described in C. Zhang et al, *J. Immunol.*, 57:3980–3987 (1996), which is incorporated by reference herein for its description and characterization of this antigen.

In summary, a panel of monoclonal antibodies was raised against dying cells by immunizing mice with apoptotic Jurkat cells. One of these antibodies, anti-7A6 (later named APO2.7), was found to react with apoptotic cells. As determined by flow cytometry and ELISA, no reactivity of APO2.7 was observed in normal or digitonin-permeabilized human peripheral blood lymphocytes; nor was any reactivity observed in tested lymphoid cell lines. The antibody, however, reacted strongly with these cells when they were induced to undergo apoptosis by irradiation or treatment with other apoptosis-inducing agents. Cell sorting and DNA fragmentation experiments revealed that 7A6+ cells but not 7A6– cells, had apparent DNA fragments characteristic of cells undergoing apoptosis. By immunoblot under reducing conditions APO 2.7 detected a 38 kD protein band in the cell lysates prepared from apoptotic cells. Immunoelectron microscopy showed the 7A6 antigen to be localized to the membrane of mitochondria in apoptotic Jurkat cells. These results indicate that 7A6 is a novel epitope on the mitochondrial membrane protein which is exposed on cells undergoing apoptosis, indicated that the 7A6 molecule.

Making use of this information, one of skill in the art can readily obtain the 7A6 antigen by the means described therein, or by other suitable means, and utilize the antigen for production of antibodies. Suitable techniques for generating monoclonal antibodies are well known to those of skill in the art. See, e.g., Kohler and Milstein, *Nature*, 256:495–497 (1975). Techniques for producing other suitable antibodies, including polyclonal antibodies and synthetic antibodies are also known in the art. See, e.g., Harlow et al, *Antibodies: A Laboratory Manual*, Cold Spring Harbor Laboratory (1988).

Most preferably, the anti-apoptotic-associated binding protein utilized in the method of the invention is the anti-7A6 antibody, APO2.7, which has been described [C. Zhang et al, cited above, which is incorporated by reference herein]. The hybridoma cell line expressing this antibody has been deposited with the American Type Culture Collection, 10801 University Boulevard, Manassas, Va. 20110-2209 (USA) under ATCC Accession No. HB 12065, pursuant to the provisions of the Budapest Treaty.

For convenience throughout this specification, reference will be made to the APO2.7 antibody. However, the skilled artisan will understand from the foregoing, that the above-defined anti-apoptotic-associated binding proteins may be substituted for APO2.7 in the methods described herein.

According to the method of the invention, following staining with anti-tubulin and the first labeled APO2.7 antibody, the cells are permeabilized using conventional techniques. Currently, the preferred method of permeabilization involves incubation with digitonin as described [Fiskum et al., 1980, *Proc. Natl. Acad. Sci. USA*, 77:3430–3434; Anderson et al., 1989, *J. Immunol,*. 143:1899–1904). It is currently preferred for this incubation to be performed on ice for between about 5 minutes to about 30 minutes, and most preferably for about 20 minutes. However, the skilled artisan can readily adjust these conditions, as needed or required. Although less desirable, other means of cell permeabilization may be utilized in the method of the invention. For example, the cells may be permeabilized by incubation with 0.05% to 0.1% paraformaldehyde prior to incubation with digitonin. The means of permeabilization are not a limitation on the present invention.

Following permeabilization, the cells are then contacted with a second labeled binding protein (e.g., APO2.7). This binding protein may be same or different from the first labeled binding protein used in this method. However, the method requires that the binding protein be labeled in a manner which permits the cells or cell fractions which bind this labeled binding protein (and are thus stained) to be distinguished from the cells stained with the first labeled binding protein prior to permeabilization. For example, as illustrated herein, when the first label utilized for the apoptosis-associated antigen is PE, the second apoptosis-associated antigen may be labeled with PECy5. Suitably, these labels are also distinguishable, e.g., colorimetrically, from the label used on the anti-tubulin.

The cells are analyzed to identify, either quantitatively or qualitatively, viable cells, early apoptotic cells, late apoptotic cells, and necrotic cells by distinguishing the cells labeled with anti-tubulin and each of the anti-apoptotic-associated antigen binding proteins, before and after permeabilization. Suitable analysis techniques may be readily selected by one of skill in the art and include immunohistochemistry methods, and fluorometric techniques.

Most preferably, this analysis is conducted using multicolor immunofluorescence. Such techniques are well known and may be readily performed using commercially available flow cytometers, such as those available from Coulter. Briefly described, in flow cytometry, the sample is subjected to a stable light beam of a known wavelength, and the cell subsets detected by fluorescence or light scattering from cells. The light scatter characteristics of the target cells of interest are then compared to the light scatter characteristics of normal or control cells. Generally, the cytometer "gates" only cells of interest, thereby excluding other cells or particles. The flow cytometric data are then displayed as a histogram of the digitized data.

Among the collected anti-tubulin-stained cells, those labeled with the first APO2.7 vs. the second labeled APO2.7 antibody are compared, permitting the viable, early apoptotic, late apoptoticic and necrotic cells to be distinguished. More particularly, as described in Example 1 below, during this flow cytometry analysis, cells which are positively stained for anti-tubulin are gated, thus providing the cells in the sample which are late apoptotic and necrotic, i.e., have disrupted membranes. Cells which are negative for anti-tubulin are also gated, thus distinguishing cells which are either normal (i.e., viable) or early apoptotic. The use of the APO2.7 antibody permits normal cells to be distinguished from those which are in the early stages of apoptosis (i.e., positive for APO2.7). More particularly, anti-tubulin negative cells which are stained with the second labeled APO2.7 antibody (i.e., post-permeabilization) are early apoptotic and those non-stained with the first and second labeled APO2.7 antibody are normal, viable cells. Anti-tubulin positive cells which are stained with the first and second labeled APO2.7 antibody are late apoptotic; anti-tubulin positive cells which are non-stained with either the first or the second labeled APO2.7 antibody are necrotic cells.

The method of the invention permits the viable, early apoptotic, late apoptotic and necrotic cells to be identified both quantitatively and qualitatively. This information is useful for a variety of purposes, which include basic and clinical research. For example, the method of the invention permits one to monitor the status of a patient's response to treatment for such conditions as HIV and leukemia, among others. Other uses will be readily apparent to those of skill in the art.

The following examples illustrate the preferred methods for performing the assay of the invention. As described above, other suitable means of analyzing the labeled cells may be readily determined by one of skill in the art and the parameters adjusted accordingly. These examples are illustrative only and do not limit the scope of the invention.

EXAMPLE 1

Cell Preparation and Staining

For use in the following experiment, normal or apoptotic Jurkat cells induced by the anti-CD95 antibody 7C11 [Coulter].

Cells are first stained with anti-tubulin-FITC conjugated antibody and anti-APO2.7-PE conjugated antibody, and incubated for 15 minutes at room temperature (RT), protected from the light. After washing, cells are permeabilized in 100 μg/ml digitonin solution in PBS, by incubating for 20 minutes on ice. Cells are washed, and finally stained with APO2.7-PECy5 conjugated antibody. After a final wash, 1.0 ml of PBSF is added and cells are stored on ice, protected from light until analyzed on the flow cytometer.

EXAMPLE 2

Flow Cytometric Analysis

The cells stained according to the method of the invention, as described in Example 1, were analyzed by flow cytometry.

A. Instrument Configuration

Excitation of all three fluorochromes is accomplished simultaneously on a COULTER EPICS ELITE, ESP flow cytometer using a single argon-ion laser. [The present invention is not limited to any particular flow cytometer; other commercially available flow cytometers may be used to perform this analysis.] Signal discrimination was on forward scatter. The FITC, PE, and PECy5 fluorescence emissions are initially split using a 550-nm dichroic longpass filter, with FITC collected through a 525-nm bandpass filter. PE and PECy5 are further split using a 600-nm dichroic longpass filter with PE and PECy5 collected through 575-nm and 675-nm bandpass filters, respectively. Due to the nature of overlapping PE and FITC fluorescence spectra, electronic compensation is applied to both the FITC and the PE fluorescence signals that are collected in their respective fluorescence detectors. Electronic compensation must be applied to remove the overlapping FITC signal in the PE signal, and overlapping PE signal in the FITC signal.

B. Data Analysis

Figure 1C:
FIG. 1C is a histogram illustrating the results following performance of the method of the invention and gating on anti-tubulin negative cells. The lower left quadrant shows viable cells and the lower right quadrant shows early apoptotic cells.
Figure 1C:
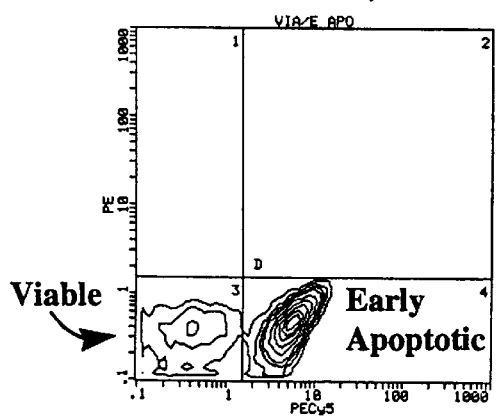
Figure 1D:
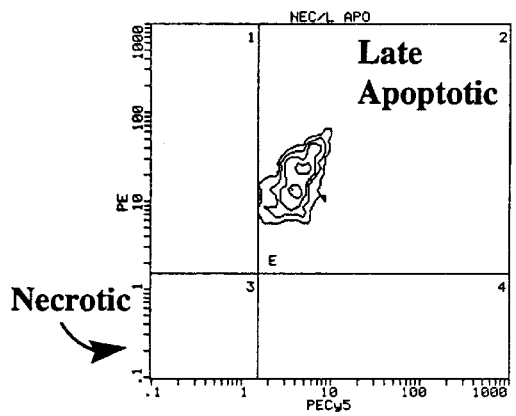
FIG. 1D is a histogram illustrating the results following performance of the method of the invention and gating on anti-tubulin positive cells. The upper right quadrant shows late apoptotic cells and the lower left quadrant shows this sample contained no necrotic cells.

A histogram illustrating light scatter from the cells to be analyzed is provided in FIG. 1A. A single parameter anti-tubulin-FITC histogram is collected with a gate on light scatter. See, FIG. 1B. Two dual parameter APO2.7-PECy5 vs. APO2.7-PE histograms are then collected, one gated on the negative portion, and one gated on the positive portion, of the anti-tubulin-FITC histogram. The former histogram identifies viable and early apoptotic cells (FIG. 1C); whereas the latter histogram identifies necrotic and late apoptotic cells (Fig. ID). As can be observed in Fig. ID, the sample used in this experiment contained no necrotic cells.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for identifying viable cells, cells in the early stages of apoptosis, cells in the late stages of apoptosis, and necrotic cells, said method comprising the steps of:
   (a) providing a first binding protein specific for an intracellular eukaryotic protein, said first protein labeled with a first visually detectable label,
   (b) providing a second binding protein specific for an apoptosis-associated antigen, said second protein labeled with a second visually detectable label, said second label distinguishable from said first label;
   (c) providing a third binding protein specific for an apoptosis-associated antigen, said third protein labeled with a third visually detectable label, said third label distinguishable from said first and said second labels;
   (d) contacting a sample of cells with said first protein (a), wherein said protein (a) labels necrotic cells and late apoptotic cells with said first label, leaving viable cells and early apoptotic cells unlabeled by said first label;
   (e) contacting said sample of (d) with said second labeled protein (b), wherein said protein (b) labels late apoptotic cells with said second label, leaving viable cells, necrotic cells and early apoptotic cells unlabeled with said second label;
   (f) permeabilizing the cells of said sample from step (e);
   (g) contacting said permeabilized cells with said third labeled protein (c), wherein said protein (c) labels early apoptotic and late apoptotic cells with said third label, said necrotic cells and viable cells unlabeled with said third label; and
   (h) analyzing the cells by flow cytometry and identifying the cells by the pattern of labeling, wherein viable cells are unlabeled, necrotic cells are labeled with only said first label, early apoptotic cells are labeled with only said third label, and late apoptotic cells are labeled with the first, second and third detectable labels.

2. The method according to claim 1, wherein the apoptosis-associated antigen of (b) or (c) is the 7A6 antigen to which APO2.7 binds.

3. The method according to claim 1, wherein the second and third binding proteins are independently selected from the group consisting of antibodies, F(ab')2 fragments, Fab' fragments, and Fv fragments.

4. The method according to claim 1, wherein the second and third binding proteins are directed to the same apoptosis-associated antigen.

5. The method according to claim 1, wherein the second binding protein is monoclonal antibody APO2.7, which is specific for the apoptosis-associated antigen 7A6.

6. The method according to claim 5, wherein the eukaryotic binding protein is anti-tubulin.

7. The method according to claim 1, wherein the intracellular eukaryotic binding protein is directed against a protein selected from the group consisting of tubulin, cytokeratin, actin and microtubule-associated proteins.

8. The method according to claim 1, wherein the first visually detectable label is PE, the second visually detectable label is PECy5, and the third visually detectable label is FITC.

9. The method according to claim 1, wherein the cells are permeabilized with digitonin.

10. The method according to claim 1, further comprising the step of gating cells positive for the intracellular eukaryotic protein and identifying the cells stained by the second and third labeled binding proteins, wherein the cells stained with the second and third labeled binding proteins are late apoptotic and the cells unstained by said labeled binding proteins are necrotic.

11. The method according to claim 1, further comprising the step of gating cells negative for the intracellular eukaryotic protein and identifying the cells stained by the labeled second and third labeled binding proteins, wherein the cells stained by the labeled third binding protein are early apoptotic cells and the un-stained cells are the viable cells.

12. The method according to claim 1, wherein the visually detectable labels are fluorochromes.

13. The method according to claim 12, wherein the detectable labels are PE, PECy5, and FITC.

14. A method for identifying viable cells, cells in the early stages of apoptosis, cells in the late stages of apoptosis, and necrotic cells, said method comprising the steps of:
   (a) providing a first binding protein labeled with a first visually detectable label, wherein said first binding protein is specific for an intracellular eukaryotic protein;
   (b) providing a second binding protein labeled with a second visually detectable label which is distinguishable from said first label, wherein said second binding protein is selected from the group of the monoclonal antibody APO2.7 which is specific for the apoptosis-associated antigen 7A6, and antigen binding fragments thereof;
   (c) providing a third binding protein labeled with a third visually detectable label which is distinguishable from said first and second labels, wherein said third binding protein is selected from the group of the monoclonal antibody APO2.7 and antigen binding fragments thereof;
   (d) contacting a sample of cells with said first labeled binding protein (a), wherein said first binding protein labels necrotic cells and late apoptotic cells with said first label, leaving viable cells and early apoptotic cells unlabeled by said first label;
   (e) contacting said sample of (d) with said second labeled binding protein (b), wherein said binding protein (b) labels late apoptotic cells with said second label, leaving viable cells, necrotic cells and early apoptotic cells unlabeled with said second label;
   (f) permeabilizing the cells of said sample from step (e);
   (g) contacting said permeabilized cells with said third binding protein (c), wherein said third binding protein (c) labels early apoptotic and late apoptotic cells with said third label, said necrotic cells and viable cells unlabeled with said third label; and
   (h) analyzing the cells by flow cytometry and identifying the cells by the pattern of labeling, wherein viable cells are unlabeled, necrotic cells are labeled with only said first label, early apoptotic cells are labeled with only said third label, and late apoptotic cells are labeled with the first, second and third detectable labels.

15. The method according to claim 14, wherein the intracellular eukaryotic binding protein is directed against a protein selected from the group consisting of tubulin, cytokeratin, actin and microtubule-associated proteins.

16. The method according to claim 14, wherein the second or third binding protein is an antigen binding fragment of APO2.7, each independently selected from the group consisting of F(ab')2 fragments, Fab' fragments and Fv fragments.

17. The method according to claim 14, further comprises the step of gating cells positive for the intracellular eukaryotic protein and identifying the cells stained by the second and third labeled binding proteins, wherein the cells stained with the second and third labeled binding proteins are late apoptotic and the cells unstained by labeled binding proteins are necrotic.

18. The method according to claim 14, further comprising the step of gating cells negative for the intracellular eukaryotic protein and identifying the cells stained by the labeled second and third labeled binding proteins, wherein the cells stained by the labeled second and third binding proteins are early apoptotic cells and the unstained cells are the viable cells.

19. A method for distinguishing viable cells, cells in the early stage of apoptosis, cells in the late stage of apoptosis, and necrotic cells, said method comprising the steps of:

(a) staining a sample of cells with anti-tubulin-fluorescein isothiocyanate (FITC), thereby providing positive and negative anti-tubulin-FITC populations;

(b) staining the cells with APO2.7, the monoclonal antibody specific for the apoptosis-associated antigen 7A6, labeled with phycoerythrin (PE);

(c) permeabilizing the cells with digitonin;

(d) staining the cells with APO2.7 labeled with phycoerythrin-cyanin dye 5 (ECy5); and (e) analyzing the cells by flow cytometry to distinguish viable cells, early apoptotic cells; late apoptotic cells, and necrotic cells, wherein viable cells are unlabeled, necrotic cells are labeled with only FITC, early apoptotic cells are labeled with only PECy5, and late apoptotic cells are labeled with FITC, PE, and PECy5.

* * * * *